United States Patent
Zhang et al.

(10) Patent No.: US 9,758,740 B2
(45) Date of Patent: Sep. 12, 2017

(54) METHOD AND DEVICE FOR CONVERTING CARBON DIOXIDE IN FLUE GAS INTO NATURAL GAS

(71) Applicant: Wuhan Kaidi Engineering Technology Research Institute Co., Ltd., Wuhan (CN)

(72) Inventors: Yanfeng Zhang, Wuhan (CN); Yilong Chen, Wuhan (CN); Zhilong Wang, Wuhan (CN); Zhangjian Fang, Wuhan (CN); Xingcai Zheng, Wuhan (CN)

(73) Assignee: WUHAN KAIDI ENGINEERING TECHNOLOGY RESEARCH INSTITUTE CO., LTD., Wuhan (CN)

( * ) Notice: Subject to any disclaimer, the term of this patent is extended or adjusted under 35 U.S.C. 154(b) by 21 days.

(21) Appl. No.: 14/920,907

(22) Filed: Oct. 23, 2015

(65) Prior Publication Data

US 2016/0040084 A1 Feb. 11, 2016

Related U.S. Application Data

(60) Division of application No. 14/522,625, filed on Oct. 24, 2014, now Pat. No. 9,193,927, which is a (Continued)

(30) Foreign Application Priority Data

Apr. 24, 2012 (CN) .......................... 2012 1 0121972

(51) Int. Cl.
*B01J 7/00* (2006.01)
*C10L 3/00* (2006.01)
*C10L 3/06* (2006.01)
*C10L 3/08* (2006.01)
*C07C 1/00* (2006.01)
(Continued)

(52) U.S. Cl.
CPC . *C10L 3/08* (2013.01); *B01J 7/00* (2013.01); *C07C 1/12* (2013.01); *C10L 3/06* (2013.01); *C10L 2290/06* (2013.01); *C10L 2290/10* (2013.01); *C10L 2290/38* (2013.01); (Continued)

(58) Field of Classification Search
CPC ...... B01J 7/00; C10L 3/00; C10L 3/06; C10L 3/08; C10L 2290/00; C10L 2290/06; C10L 2290/10; C10L 2290/38; C10L 2290/42; C10L 2290/54; C07C 1/00; C07C 1/02; C07C 1/12; Y02P 20/00–20/12;
(Continued)

(56) References Cited

U.S. PATENT DOCUMENTS

2011/0284367 A1* 11/2011 Goller ..................... C23F 13/06
204/196.02
2013/0041051 A1* 2/2013 Zuberbuhler ............ B01J 8/001
518/712

* cited by examiner

*Primary Examiner* — Natasha Young
(74) *Attorney, Agent, or Firm* — Matthias Scholl P.C.; Matthias Scholl

(57) ABSTRACT

A device for converting carbon dioxide in flue gas into natural gas using dump energy. The device includes a transformer and rectifier device, an electrolytic cell, a turbine, a carbon dioxide heater, a primary fixed bed reactor, a secondary fixed bed reactor, a natural gas condenser, and a process water line. An outlet of the transformer and rectifier device is connected to a power interface of the electrolytic cell, a gas-liquid outlet of a cathode of the electrolytic cell is connected to a gas-liquid inlet of a hydrogen separator, and a liquid outlet of the hydrogen separator is connected to a liquid reflux port of the cathode of the electrolytic cell.

10 Claims, 2 Drawing Sheets

Related U.S. Application Data continuation-in-part of application No. PCT/CN2013/074228, filed on Apr. 16, 2013.

(51) Int. Cl.
*C07C 1/02* (2006.01)
*C07C 1/12* (2006.01)

(52) U.S. Cl.
CPC ....... *C10L 2290/42* (2013.01); *C10L 2290/54* (2013.01); *Y02E 60/366* (2013.01); *Y02P 20/133* (2015.11)

(58) Field of Classification Search
CPC ........ Y02P 20/133; Y02E 60/00; Y02E 60/30; Y02E 60/36; Y02E 60/366
See application file for complete search history.

METHOD AND DEVICE FOR CONVERTING CARBON DIOXIDE IN FLUE GAS INTO NATURAL GAS

CROSS-REFERENCE TO RELATED APPLICATIONS

This application is a divisional of U.S. application Ser. No. 14/522,625, now pending, which is a continuation-in-part of International Patent Application No. PCT/CN2013/074228, now WO 2013/159661, with an international filing date of Apr. 16, 2013, designating the United States, and further claims priority benefits to Chinese Patent Application No. 201210121972.7 filed Apr. 24, 2012. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND OF THE INVENTION

Field of the Invention

The invention relates to technology for energy conversion of industrial flue gas using dump energy arising from renewable energy generation, and specifically relates to a method and a device for converting carbon dioxide in flue gas into natural gas by dump energy.

Description of the Related Art

There is an ongoing need to make full use of the dump energy arising from renewable energy generation and further to effectively reduce the greenhouse effect.

SUMMARY OF THE INVENTION

It is one objective of the invention to solve the defects of renewable energy generation such as grid connection obstacles or being difficult to store short-time dump energy, and the problem that fossil energy has environmental pollution caused by greenhouse gas, and provide a method and a device for converting carbon dioxide in flue gas into natural gas by dump energy.

To achieve the above purpose, the key concept of the method designed in the invention for converting carbon dioxide in flue gas into natural gas by dump energy is to first generate hydrogen through water electrolysis using pump energy, and then synthesize natural gas easy for storage or transportation through methanation reaction between hydrogen and carbon dioxide trapped from industrial flue gas, which also facilitates reasonable application of carbon dioxide discharged from industrial flue gas. The method comprises the following steps:

1) transforming and rectifying a voltage of dump energy generated from a renewable energy plant, introducing the voltage-transformed and rectified dump energy into an electrolyte solution to electrolyze water therein to yield $H_2$ and $O_2$, and drying $H_2$;
2) purifying industrial flue gas to separate $CO_2$ therein and purifying $CO_2$;
3) transporting $H_2$ generated from step 1) and $CO_2$ from step 2) to a synthesis equipment comprising at least two fixed bed reactors, allowing a methanation reaction between $H_2$ and $CO_2$ to happen to yield a high-temperature mixed gas with main ingredients of $CH_4$ and water vapor;
4) employing the high-temperature mixed gas generated from step 3) to conduct indirect heat exchange with process water to yield superheated water vapor;
5) delivering the superheated water vapor generated from step 4) to a turbine to generate electric energy, and returning the electric energy to step 1) for water electrolysis; and
6) condensing and drying the mixed gas in step 4) cooled through the indirect heat exchange, until natural gas with $CH_4$ content up to the standard is obtained.

The natural gas (SNG) can be sent to the existing natural gas pipe network through pressurized transport, or pressurized to liquefied natural gas (LNG) for transport.

In a class of this embodiment, in step 1), the renewable energy is selected from solar energy, hydroenergy, wind energy, or a combination thereof. These renewable energies are the most environment-friendly, cheapest and safest. The electrolyte solution is preferably potassium hydroxide solution or other similar solutions with the density of 1.2-1.4 kg/m$^3$. Reaction temperature of the electrolyte solution is controlled at 90±2° C., and the reaction mechanism of water electrolysis is as follows: $2H_2O=2H_2\uparrow+O_2\uparrow$. Compared with the pure water, the electrolyte solution can significantly lower the electrolytic reaction temperature, and save power consumption. After moisture removal and cooling of the resulting $H_2$ and $O_2$, $H_2$ may be used for the reaction in the next step, while $O_2$ may be as a by-product for other usage.

In a class of this embodiment, various parameters of the fixed bed reactor at every stage in the above step 3) are as follows: inlet temperature: 250-300° C., reaction pressure: 3-4 MPa, outlet temperature: 350-700° C. Methanation reaction mechanism of $H_2$ and $CO_2$ is as follows: $4H_2+CO_2=CH_4+2H_2O+4160$ kj/kg·$CO_2$. In specific operation, generally their mixture at a volume ratio of $H_2:CO_2=4:1$ is transferred to a fixed bed reactor for strong exothermic reaction in the presence of a nickel-based catalyst or a similar catalyst, whilst releasing a lot of heat, so that the temperature of the resulting mixed gas is greatly improved. At least two stage fixed bed reactors are provided to ensure complete reaction between $H_2$ and $CO_2$, and improve the utilization efficiency of $H_2$.

In a class of this embodiment, in step 3), part of the high-temperature mixed gas from the primary fixed bed reactor is bypassed for cooling, water removal, pressurization and heating, and is then mixed with fresh $H_2$ and $CO_2$, so that the mixed gas is transported back to the primary fixed bed reactor after the volume content of $CO_2$ therein is 6-8%. In this way, on the one hand, fresh $H_2$ and $CO_2$ can be preheated with returning high-temperature gas to save energy consumption; on the other hand, the reaction heat can be controlled through adjusting the volume content of $CO_2$, thereby controlling the highest outlet temperature of the fixed bed reactor, so that the catalyst is not deactivated at allowed temperature to ensure stable operation of the fixed bed reactor.

In a class of this embodiment, in a step 4), firstly, the process water is heated to superheated water, which is then converted to yield water vapor, and finally the water vapor is converted to yield superheated water vapor. In this way, the process water is continuously, stably and reliably converted to yield superheated water vapor, so as to ensure that the turbine always uninterruptedly generates power. The electric energy generated thereby continues to be used for water electrolysis, so that the high heat generated from the methanation reaction is fully used to improve the conversion efficiency of the renewable energy.

In a class of this embodiment, in step 5), the steam exhaust generated by the turbine after being driven for power generation is condensed to water, and then sent back to the process water line for recycling, so as to effectively improve the utilization efficiency of the process water, and save water resources.

In a class of this embodiment, in step 6), condensed water from the mixed gas is transported back to the process water line for recycling, which can effectively improve the utilization efficiency of the process water, and save water resources.

To achieve the above objectives, the invention also provides a device for converting carbon dioxide in flue gas into natural gas using dump energy. The device comprises a transformer and rectifier device, an electrolytic cell, a turbine, a carbon dioxide heater, a primary fixed bed reactor, a secondary fixed bed reactor, a natural gas condenser, and a process water line. An outlet of the transformer and rectifier device is connected to a power interface of the electrolytic cell, a gas-liquid outlet of a cathode of the electrolytic cell is connected to a gas-liquid inlet of a hydrogen separator, a liquid outlet of the hydrogen separator is connected to a liquid reflux port of the cathode of the electrolytic cell, a $H_2$ outlet of the hydrogen separator is connected to an inlet of a hydrogen cooler, both the outlet of the hydrogen cooler and outlet of the carbon dioxide heater are connected to an inlet of the primary fixed bed reactor, an outlet of the primary fixed bed reactor is connected to an inlet of the secondary fixed bed reactor successively through the superheater and mixed gas line of the primary heat exchanger, and the outlet of the secondary fixed bed reactor is connected to the inlet of the natural gas condenser successively through the secondary heat exchanger and the mixed gas line of the preheater. The process water line is connected to the aqueous medium inlet of the preheater, the aqueous medium outlet of the preheater is connected to the steam inlet of the superheater through a steam pocket, the steam outlet of the superheater is connected to the steam inlet of the turbine, and the electric outlet of the turbine is connected to the inlet of the transformer and rectifier device.

In a class of this embodiment, the mixed gas outlet of the primary heat exchanger is still provided with a bypass connected to the heat medium inlet of a circulating heat exchanger, the heat medium outlet of the circulating heat exchanger is connected to the inlet of a circulating compressor through a circulating cooler, the outlet of the circulating compressor is connected to the heated medium inlet of the circulating heat exchanger, and the heated medium outlet of the circulating heat exchanger is connected to the inlet of the primary fixed bed reactor. In this way, a part of the high-temperature mixed gas generated from the reaction can reenter the primary fixed bed reactor by means of self-circulation, so as to realize preheating the fresh $H_2$ and $CO_2$, reduce energy consumption and ensure continuous reaction.

In a class of this embodiment, an intermediate fixed bed reactor is also provided between the above primary fixed bed reactor and secondary fixed bed reactor. The inlet of the intermediate fixed bed reactor is connected to the mixed gas outlet of the primary heat exchanger, and the outlet of the intermediate fixed bed reactor is connected to the inlet of the secondary fixed bed reactor through an intermediate heat exchanger. In this way, in fact, three stage fixed bed reactors are provided, so as to distribute the methanation reaction rate of $H_2$ and $CO_2$ stage by stage, until complete reaction of the raw materials. At the same time, temperature of the fixed bed reactor can be reduced stage by stage, so as to obtain different quality of steam (temperature, pressure), and meet the needs of the turbine.

In a class of this embodiment, the steam exhaust outlet of the above turbine is connected to the process water line through the steam exhaust condenser, which can save the water resources, and improve the utilization rate of process water.

In a class of this embodiment, the above process water line is still connected to the gas-liquid inlet of the hydrogen separator. In this way, water can be transported to the electrolytic cell by the hydrogen separator to supplement the water losses in the electrolytic reaction process and cool the heat generated from the water electrolysis process.

In a class of this embodiment, the condensed water outlet of the above natural gas condenser is connected to the aqueous medium inlet of the preheater, so as to save the water resources, and improve the utilization rate of process water.

Advantages according to embodiments of the invention are summarized as follows.

First, carbon dioxide trapped from industrial flue gas is converted to yield methane fuel (i.e., the main ingredient of natural gas) convenient for storage and transport through methanation reaction with hydrogen generated from water electrolysis by dump energy arising from the renewable energy generation, such as solar energy, hydroenergy, and wind energy etc. In this way, methane fuel is easily introduced into the existing natural gas pipe network system, and may also be pressurized to liquefied natural gas (LNG) for transport by tank cars, thereby effectively solving the above grid connection obstacle of dump energy or problem of difficult storage of short-term dump energy.

Second, in the process of synthesizing methane using hydrogen and carbon dioxide, huge amounts of carbon dioxide in flue gas is utilized, thereby achieving the goal of reducing carbon dioxide emission, solving the problem of reducing huge amounts of carbon dioxide emission generated by fossil fuel, and bringing great economic benefits and social benefits.

Third, methanation reaction of hydrogen and carbon dioxide is a strong exothermic reaction, huge amounts of heat will be released in the process, the heat energy is used to produce high-temperature superheated steam to continue power generation, and then the electric energy is used for circulation of water electrolysis, thereby greatly improving the conversion efficiency of renewable energy.

Fourth, only methane and water vapor as the natural gas fuel are present in the end product of methanation reaction of hydrogen and carbon dioxide, and no other toxic by-products are available, which can not only ensure the quality of the natural gas, but also reduce environment pollution caused by greenhouse gas.

DETAILED DESCRIPTION OF THE EMBODIMENTS

The method and device in the invention are further illustrated in detail in the light of the drawings and specific embodiments as follows:

Example 1

Figure 1:
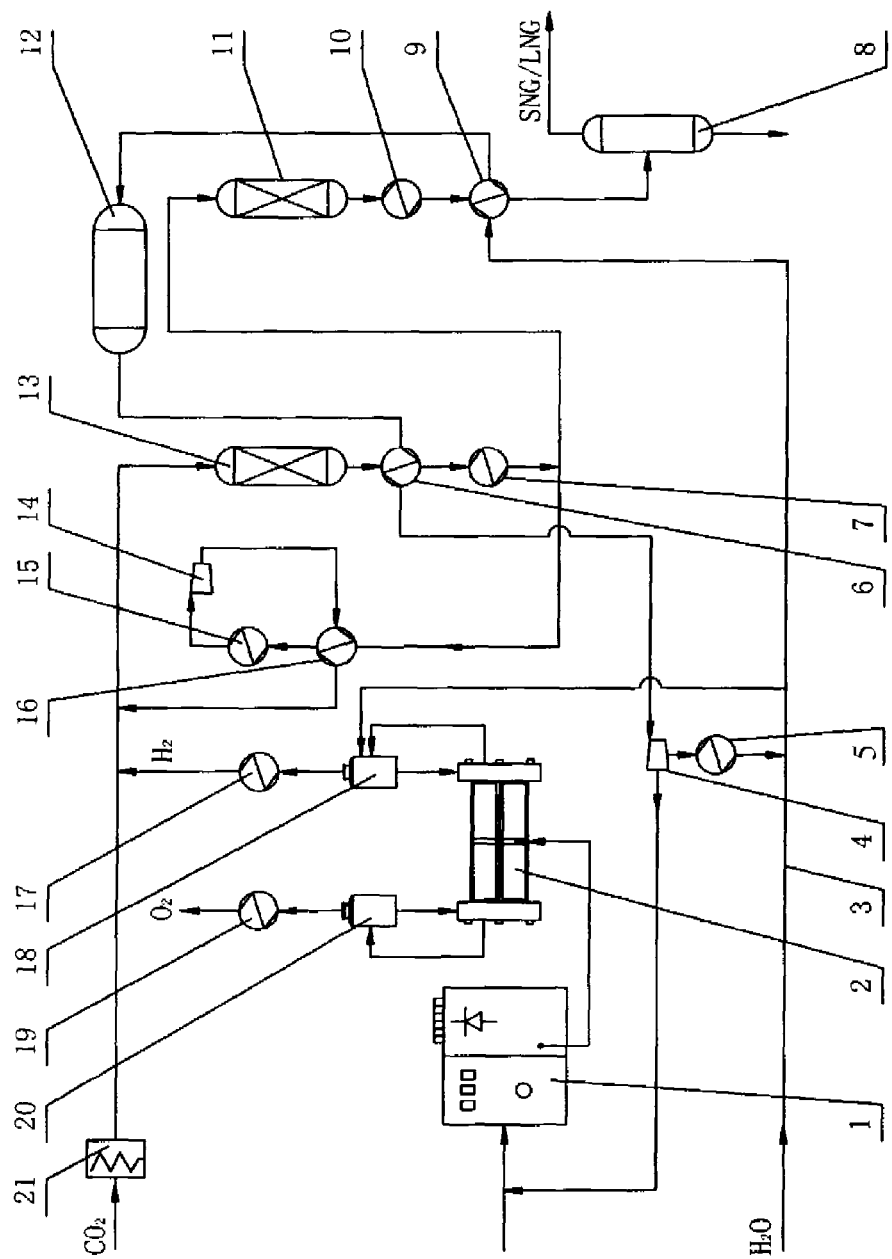
FIG. 1 is a structural diagram of a device for converting carbon dioxide in flue gas into natural gas by dump energy.

A device for converting carbon dioxide into natural gas by dump energy, as shown in FIG. 1, comprises a transformer and rectifier device 1, an electrolytic cell 2, a turbine 4, a carbon dioxide heater 21, a primary fixed bed reactor 13, a secondary fixed bed reactor 11, a natural gas condenser 8 and a process water line 3. The outlet of the transformer and rectifier device 1 is connected to the power interface of the electrolytic cell 2. The gas-liquid outlet of the anode of the electrolytic cell 2 is connected to the gas-liquid inlet of the oxygen separator 20, liquid outlet of the oxygen separator 20 is connected to the liquid reflux port of the anode of the electrolytic cell 2, $O_2$ outlet of the oxygen separator 20 is connected to the inlet of the oxygen cooler 19, and outlet of the oxygen cooler 19 is connected to a pressurized tank car or a filling device of $O_2$ (not shown in the figure) for other industrial use. The gas-liquid outlet of the cathode of the electrolytic cell 2 is connected to the gas-liquid inlet of the hydrogen separator 18, and the gas-liquid inlet of the hydrogen separator 18 is also connected to the process water line 3 to supplement water losses. The liquid outlet of the hydrogen separator 18 is connected to the liquid reflux port of the cathode of the electrolytic cell 2, $H_2$ outlet of the hydrogen separator 18 is connected to the inlet of the hydrogen cooler 17, outlet of the hydrogen cooler 17 is connected to the outlet of the carbon dioxide heater 21 and also connected to the inlet of the primary fixed bed reactor 13, so as to transport fresh $H_2$ and $CO_2$ to the primary fixed bed reactor 13.

Outlet of the primary fixed bed reactor 13 is connected to the inlet of the secondary fixed bed reactor 11 successively through a superheater 6 and mixed gas line of a primary heat exchanger 7, the mixed gas outlet of the primary heat exchanger 7 is still provided with a bypass connected to the heat medium inlet of a circulating heat exchanger 16, the heat medium outlet of the circulating heat exchanger 16 is connected to the inlet of a circulating compressor 14 through a circulating cooler 15, the outlet of the circulating compressor 14 is connected to the heated medium inlet of the circulating heat exchanger 16, and the heated medium outlet of the circulating heat exchanger 16 is connected to the inlet of the primary fixed bed reactor 13.

Outlet of the secondary fixed bed reactor 11 is successively connected to the inlet of a natural gas condenser 8 through a secondary heat exchanger 10 and mixed gas line of a preheater 9. The process water line 3 is connected to the aqueous medium inlet of the preheater 9, aqueous medium outlet of the preheater 9 is connected to the steam inlet of the superheater 6 through a steam pocket 12, the steam outlet of the superheater 6 is connected to the steam inlet of a turbine 4, and the steam exhaust outlet of the turbine 4 is connected to the process water line 3 through a steam exhaust condenser 5, and the electric outlet of the turbine 4 is connected to the inlet of the transformer and rectifier device 1 to provide electric energy for water electrolysis. In addition, the condensed water outlet of the natural gas condenser 8 may also be connected to the aqueous medium inlet of the preheater 9 (not shown in the figure) to send the condensed water back to the system for recycling.

The process flow of the above device for converting carbon dioxide in flue gas into natural gas by dump energy is as follows:

Dump energy arising from renewable energy generation, such as solar energy, hydroenergy or wind energy etc., is converted to required current through the transformer and rectifier device 1 to provide working power supply for the electrolytic cell 2. Potassium hydroxide solution with the density of 1.2-1.4 $kg/m^3$ is used as the electrolyte solution within the electrolytic cell 2, and the reaction temperature is controlled at 90±2° C. Here, anode and cathode of the electrolytic cell 2 respectively generate $O_2$ and $H_2$ carrying the electrolyte solution. The electrolyte solution is removed from $O_2$ generated therein with an oxygen separator 20, and is transported back to the electrolytic cell 2 to further participate in the reaction. Afterwards, $O_2$ is cooled in an oxygen cooler 19 to 45° C. or so for water removal, and then delivered to a pressurized tank car or a filling device for industrial use. The electrolyte solution is removed from $H_2$ generated therein with a hydrogen separator 18, and is transported back to the electrolytic cell 2 to further participate in the reaction. Afterwards, $H_2$ is cooled in a hydrogen cooler 17 to 45° C. or so for water removal, and then enters the reaction in the next step. Water losses in electrolysis is introduced into the hydrogen separator 18 through the process water line 3, is then supplemented to the electrolytic cell 2, and is also used to cool the heat generated in the water electrolysis process.

Meanwhile, $CO_2$ trapped from flue gas is purified, introduced into the carbon dioxide heater 21, heated, and mixed with $H_2$ purified through water removal at the volume ratio of $H_2:CO_2=4:1$ to fresh gas, which is transported to the primary fixed bed reactor 13 for strong exothermic reaction (methanation). In order to control the reaction heat of methanation of $H_2$ and $CO_2$, certain amount of $CH_4$ may be added into the $CO_2$ heater 21 generally at the volume ratio of $H_2:CO_2:CH_4=4:1:0.5$. Addition of $CH_4$ can be stopped after the reaction is stable. The primary fixed bed reactor 13 is kept at the inlet temperature of 250-300° C., reaction pressure of 3-4 MPa, and outlet temperature of 600-700° C. In the presence of a nickel-based catalyst, most $H_2$ reacts with $CO_2$ to generate high-temperature mixed gas of $CH_4$ and water vapor. The high-temperature mixed gas is cooled to 250-300° C. successively through the superheater 6 and primary heat exchanger 7, and then divided into two parts. Where, a part of high-temperature mixed gas enters a circulating cooler 15 through the heat medium line of the circulating heat exchanger 16, cooled to 30-40° C. after heat exchange, pressurized to 3-4 MPa and heated to 180-200° C. with a circulating compressor 14, finally further heated to 250-300° C. through the heated medium line of the circulating heat exchanger 16, and mixed with fresh $H_2$ and $CO_2$ at such a ratio that the volume content of $CO_2$ in the mixed gas is 6-8%. The mixed gas is transported to the primary fixed bed reactor 13, and the cycle is repeated. Preheating fresh $H_2$ and $CO_2$ in above circulation can greatly reduce energy consumption and control the outlet temperature of the primary fixed bed reactor 13. Another part of high-temperature mixed gas is introduced into the secondary fixed bed reactor 11, which is kept at the inlet temperature of 250-300° C., reaction pressure of 3-4 MPa, and outlet temperature of 350-500° C., so that the unreacted $H_2$ and $CO_2$ therein continue to complete the strong exothermic reaction (methanation), until complete reaction of all raw materials.

The high-temperature mixed gas of $CH_4$ and water vapor from the secondary fixed bed reactor 11 is cooled successively through a secondary heat exchanger 10 and a preheater 9, further cooled through a natural gas condenser 8, where gas $CH_4$ is cooled to 45-50° C., and flows out from the gas output of the natural gas condenser 8. $CH_4$ with the purity of more than 94% is pressurized to SNG/LNG (natural gas/liquefied natural gas), and is transported through pipeline to the existing pipe network/tank car for storage and use; while the condensed water therein flows out from the condensed water output of the natural gas condenser 8, and is transported to the aqueous medium inlet of the preheater 9 for recycling.

In the above strong exothermic reaction process of methanation, the process water is introduced into the preheater 9 through the process water line 3, and is heated to superheated water through heat exchange therein. Superheated water is transported to a steam pocket 12 through pipeline to evaporate into water vapor therein. Water vapor is transported to the superheater 6 through pipeline to convert to superheated water vapor under given pressure by further heating. The superheated vapor enters the turbine 4 through pipeline, the high-speed superheated water vapor drives the blades of the turbine 4 to rotate for power generation, the generated energy returns to the transformer and rectifier device 1 for voltage transformation, rectification, and further use for water electrolysis, so as to make full use of the waste heat in the strong exothermic reaction of methanation. The steam exhaust generated after the turbine is driven for power generation is transported to a steam exhaust condenser 5, and is condensed to water, which is transported back to the process water line 3 for recycling.

Example 2

Figure 2:
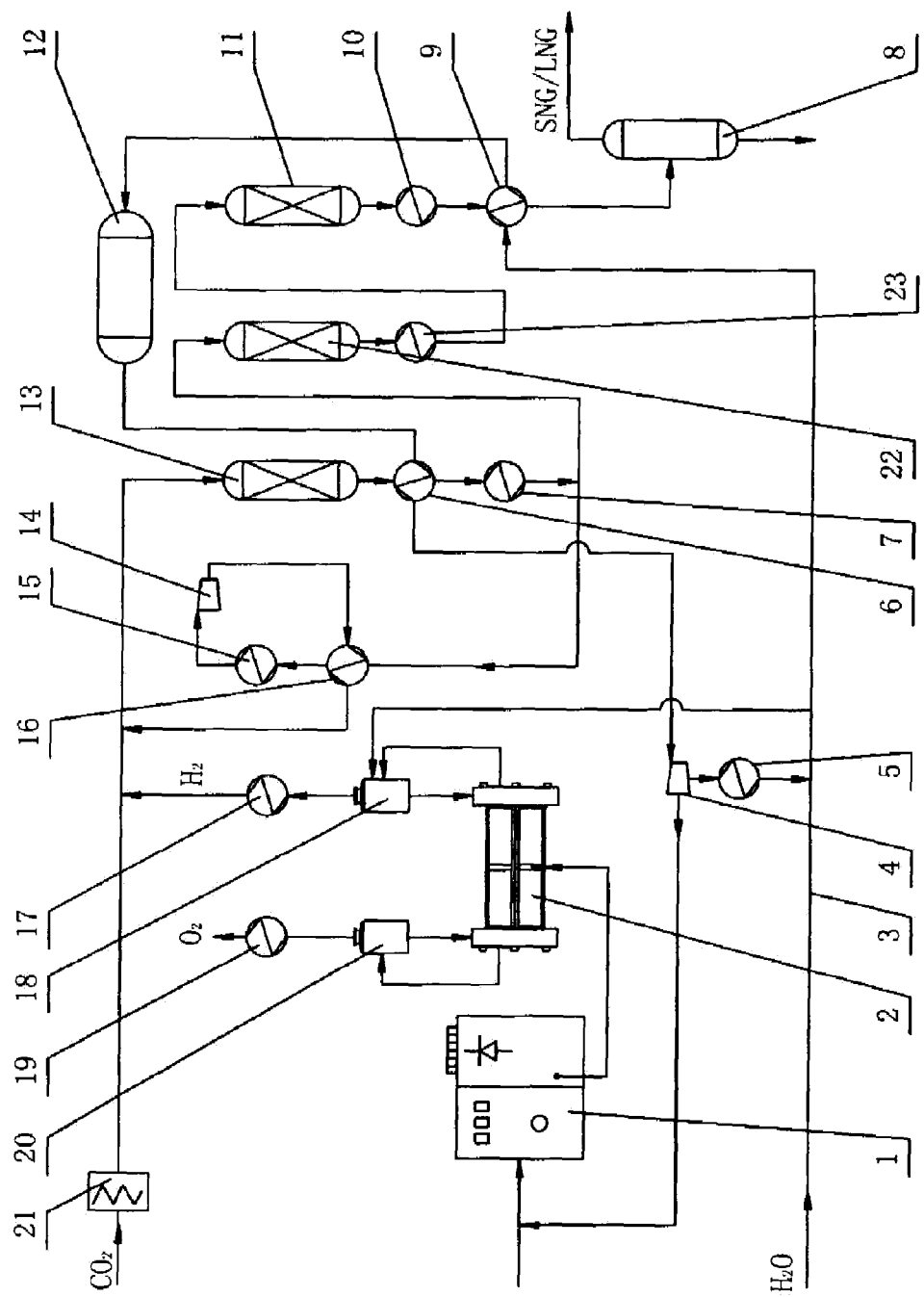
FIG. 2 is a structural diagram of another device for converting carbon dioxide in flue gas into natural gas by dump energy.

Another device for converting carbon dioxide into natural gas by dump energy, as shown in FIG. 2, has the structure and process flow basically the same as that in Example 1, except that an intermediate fixed bed reactor 22 is provided between the primary fixed bed reactor 13 and the secondary fixed bed reactor 11. The inlet of the intermediate fixed bed reactor 22 is connected to the mixed gas outlet of the primary heat exchanger 7, and the outlet of the intermediate fixed bed reactor 22 is connected to the inlet of the secondary fixed bed reactor 11 through an intermediate heat exchanger 23. In this way, three stage fixed bed reactors are provided, so as to distribute the methanation reaction rate of $H_2$ and $CO_2$ in three stages, and ensure complete reaction of the raw materials. At the same time, inlet and outlet temperature of the three stage fixed bed reactors can be reduced successively, so as to obtain corresponding quality of steam (temperature, pressure), and meet the needs of the turbine 4.

The invention claimed is:

1. A device for converting carbon dioxide in flue gas into natural gas using dump energy, the device comprising:
   a) a transformer and rectifier device;
   b) an electrolytic cell;
   c) a turbine;
   d) a carbon dioxide heater;
   e) a primary fixed bed reactor;
   f) a secondary fixed bed reactor;
   g) a natural gas condenser; and
   h) a process water line;
wherein
   an outlet of the transformer and rectifier device is connected to a power interface of the electrolytic cell, a gas-liquid outlet of a cathode of the electrolytic cell is connected to a gas-liquid inlet of a hydrogen separator, a liquid outlet of the hydrogen separator is connected to a liquid reflux port of the cathode of the electrolytic cell, a $H_2$ outlet of the hydrogen separator is connected to an inlet of a hydrogen cooler, both an outlet of the hydrogen cooler and an outlet of the carbon dioxide heater are connected to an inlet of the primary fixed bed reactor;
   an outlet of the primary fixed bed reactor is connected to an inlet of the secondary fixed bed reactor successively through a superheater and a mixed gas line of a primary heat exchanger, and an outlet of the secondary fixed bed reactor is connected to an inlet of the natural gas condenser successively through a secondary heat exchanger and a mixed gas line of a preheater; and
   the process water line is connected to an aqueous medium inlet of the preheater, an aqueous medium outlet of the preheater is connected to a steam inlet of the superheater through a steam pocket, a steam outlet of the superheater is connected to a steam inlet of the turbine, and an electric outlet of the turbine is connected to an inlet of the transformer and rectifier device.

2. The device of claim 1, wherein a mixed gas outlet of the primary heat exchanger is provided with a bypass connected to a heat medium inlet of a circulating heat exchanger, a heat medium outlet of the circulating heat exchanger is connected to an inlet of a circulating compressor through a circulating cooler, an outlet of the circulating compressor is connected to a heated medium inlet of the circulating heat exchanger, and a heated medium outlet of the circulating heat exchanger is connected to the inlet of the primary fixed bed reactor.

3. The device of claim 2, wherein an intermediate fixed bed reactor is provided between the primary fixed bed reactor and the secondary fixed bed reactor; an inlet of the intermediate fixed bed reactor is connected to the mixed gas outlet of the primary heat exchanger, and an outlet of the intermediate fixed bed reactor is connected to the inlet of the secondary fixed bed reactor through an intermediate heat exchanger.

4. The device of claim 2, wherein a steam exhaust outlet of the turbine is connected to the process water line through a steam exhaust condenser.

5. The device of claim 2, wherein the process water line is connected to the gas-liquid inlet of the hydrogen separator.

6. The device of claim 2, wherein a condensed water outlet of the natural gas condenser is connected to the aqueous medium inlet of the preheater.

7. The device of claim 1, wherein an intermediate fixed bed reactor is provided between the primary fixed bed reactor and the secondary fixed bed reactor; an inlet of the intermediate fixed bed reactor is connected to a mixed gas outlet of the primary heat exchanger, and an outlet of the intermediate fixed bed reactor is connected to the inlet of the secondary fixed bed reactor through an intermediate heat exchanger.

8. The device of claim 1, wherein a steam exhaust outlet of the turbine is connected to the process water line through a steam exhaust condenser.

9. The device of claim 1, wherein the process water line is connected to the gas-liquid inlet of the hydrogen separator.

10. The device of claim 1, wherein a condensed water outlet of the natural gas condenser is connected to the aqueous medium inlet of the preheater.

* * * * *